(12) United States Patent
Nita et al.

(10) Patent No.: US 7,604,608 B2
(45) Date of Patent: Oct. 20, 2009

(54) ULTRASOUND CATHETER AND METHODS FOR MAKING AND USING SAME

(75) Inventors: Henry Nita, Redwood City, CA (US); Jeff Sarge, Fremont, CA (US); Simon Nguyen, San Jose, CA (US)

(73) Assignee: FlowCardia, Inc., Sunnyvale, CA (US)

( * ) Notice: Subject to any disclaimer, the term of this patent is extended or adjusted under 35 U.S.C. 154(b) by 883 days.

(21) Appl. No.: 10/345,078

(22) Filed: Jan. 14, 2003

(65) Prior Publication Data

US 2004/0138570 A1 Jul. 15, 2004

(51) Int. Cl.
    *A61B 17/20* (2006.01)
(52) U.S. Cl. ....................................................... 604/22
(58) Field of Classification Search ................ 600/145, 600/146, 149; 604/265, 525, 264, 22
See application file for complete search history.

(56) References Cited

U.S. PATENT DOCUMENTS

| | | | |
|---|---|---|---|
| 3,433,226 A | 3/1969 | Boyd | |
| 3,565,062 A | 2/1971 | Kurls | |
| 3,823,717 A | 7/1974 | Pohlman et al. | |
| 4,033,331 A * | 7/1977 | Guss et al. | 600/434 |
| 4,337,090 A | 6/1982 | Harrison | |
| 4,505,767 A | 3/1985 | Quin | |
| 4,565,589 A | 1/1986 | Harrison | |
| 4,665,906 A | 5/1987 | Jervis | |
| 4,808,153 A | 2/1989 | Parisi | |
| 4,870,953 A | 10/1989 | DonMicheal et al. | |
| 4,920,954 A | 5/1990 | Alliger et al. | |
| 4,924,863 A | 5/1990 | Sterzer | |
| 4,936,281 A | 6/1990 | Stasz | |
| 5,091,205 A * | 2/1992 | Fan | 427/2.28 |
| 5,171,216 A * | 12/1992 | Dasse et al. | 604/43 |
| 5,267,954 A | 12/1993 | Nita | |

(Continued)

FOREIGN PATENT DOCUMENTS

DE            3821836 A1     2/1976

(Continued)

OTHER PUBLICATIONS

Calhoun et al., "Electron-beam systems for medical device sterilization" downloaded from web on Oct. 8, 2002 <http://www.devicelink.com/mpb/archive/97/07/002.html> 7 pages total.

(Continued)

*Primary Examiner*—Nicholas D Lucchesi
*Assistant Examiner*—Christopher D Koharski
(74) *Attorney, Agent, or Firm*—Townsend and Townsend and Crew LLP

(57) ABSTRACT

Ultrasound catheter devices and methods provide enhanced disruption of blood vessel obstructions. Generally, ultrasound catheters include an elongate flexible catheter body with one or more lumens, an ultrasound transmission member extending longitudinally through the catheter body lumen and, in some embodiments, a guidewire tube extending through the lumen. A distal head for disrupting occlusions is coupled with the distal end of the ultrasound transmission member and is positioned adjacent the distal end of the catheter body. Some embodiments include improved features such as a bend in the catheter body for enhancing positioning and/or advancement of the catheter.

16 Claims, 12 Drawing Sheets

U.S. PATENT DOCUMENTS

| | | | | |
|---|---|---|---|---|
| 5,290,229 | A | * | 3/1994 | Paskar ..................... 604/95.04 |
| 5,304,131 | A | * | 4/1994 | Paskar ..................... 604/95.04 |
| 5,312,328 | A | * | 5/1994 | Nita et al. ..................... 604/22 |
| 5,342,292 | A | | 8/1994 | Nita et al. |
| 5,380,274 | A | | 1/1995 | Nita |
| 5,382,228 | A | | 1/1995 | Nita et al. |
| 5,397,293 | A | | 3/1995 | Alliger et al. |
| 5,431,168 | A | * | 7/1995 | Webster, Jr. ................. 600/435 |
| 5,542,917 | A | * | 8/1996 | Nita et al. ..................... 604/22 |
| 5,916,192 | A | | 6/1999 | Nita et al. |
| 5,957,882 | A | | 9/1999 | Nita et al. |
| 5,957,899 | A | * | 9/1999 | Spears et al. ................. 604/264 |
| 5,964,223 | A | * | 10/1999 | Baran .................... 128/207.14 |
| 5,989,208 | A | | 11/1999 | Nita |
| 6,165,188 | A | * | 12/2000 | Saadat et al. ................. 606/159 |
| 6,287,285 | B1 | * | 9/2001 | Michal et al. ............... 604/264 |
| 6,296,620 | B1 | | 10/2001 | Gesswein et al. |
| 6,423,026 | B1 | * | 7/2002 | Gesswein et al. ............. 604/22 |
| 6,508,781 | B1 | | 1/2003 | Brennan et al. |
| 2002/0169377 | A1 | * | 11/2002 | Khairkhahan et al. ....... 600/433 |

FOREIGN PATENT DOCUMENTS

| | | |
|---|---|---|
| DE | 2438648 A1 | 1/1990 |
| EP | 316789 A2 | 5/1989 |
| EP | 316789 B1 | 5/1989 |
| WO | WO 87/05739 A1 | 9/1987 |
| WO | WO 89/06515 A1 | 7/1989 |
| WO | WO 90/01300 A1 | 2/1990 |

OTHER PUBLICATIONS

"E-Beam Theory" RDI-IBA Technology Group, downloaded from web on Oct. 8, 2002 <http://www.e-beam-rdi/EbeamTheory.htm> 2 pages total.

"Irradiation, biological, and other technologies: E-beam, biological, and sharps treatment systems" Chapter 9, Irradiation, Biological, and Other Technologies pp. 69-74.

"What is electron beam curing?" downloaded from web on Nov. 14, 2002 <http://www.ms.ornl.gov/researchgroups/composites/new%20orccmt%20pages/pages/ebwha> 4 pages total.

* cited by examiner

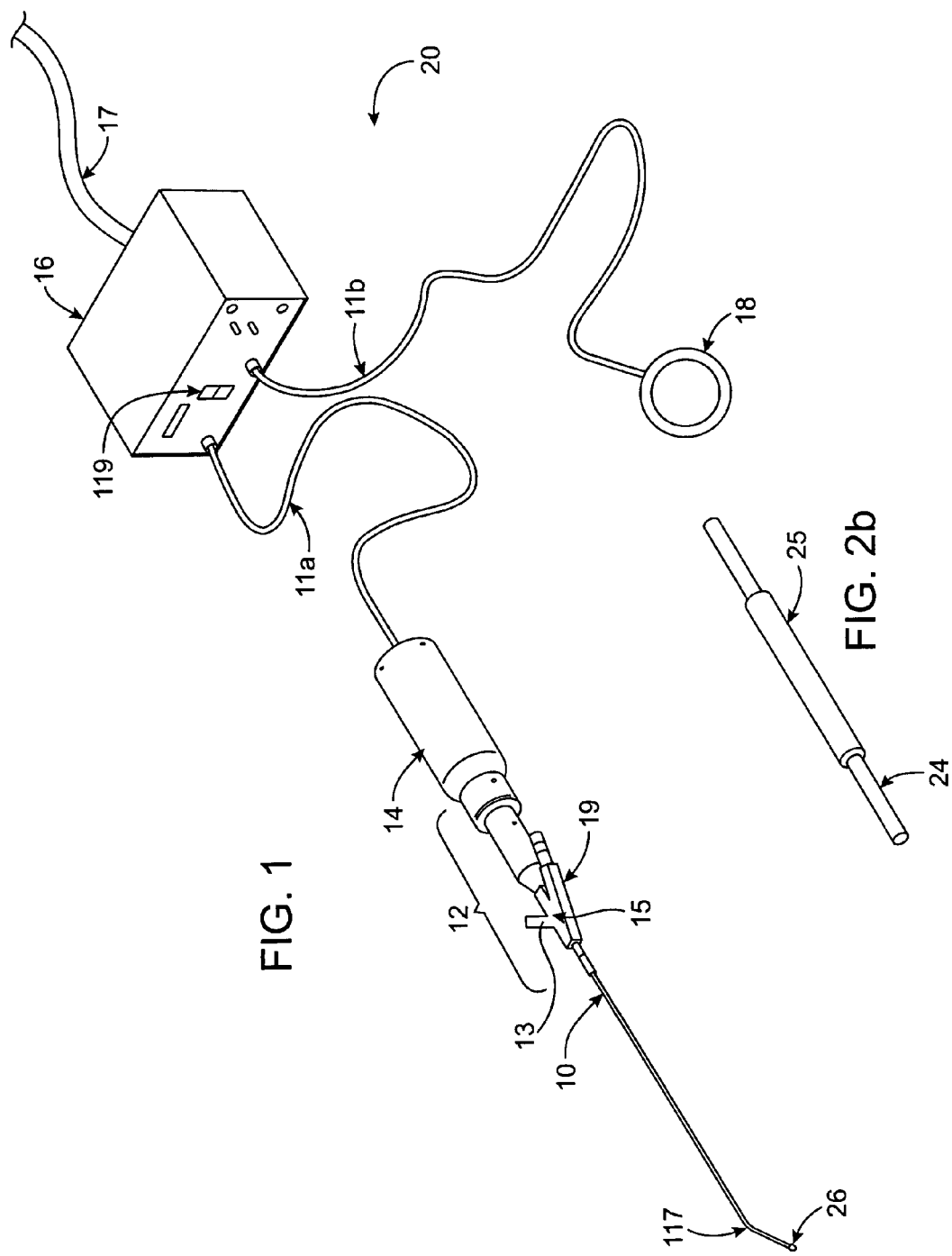

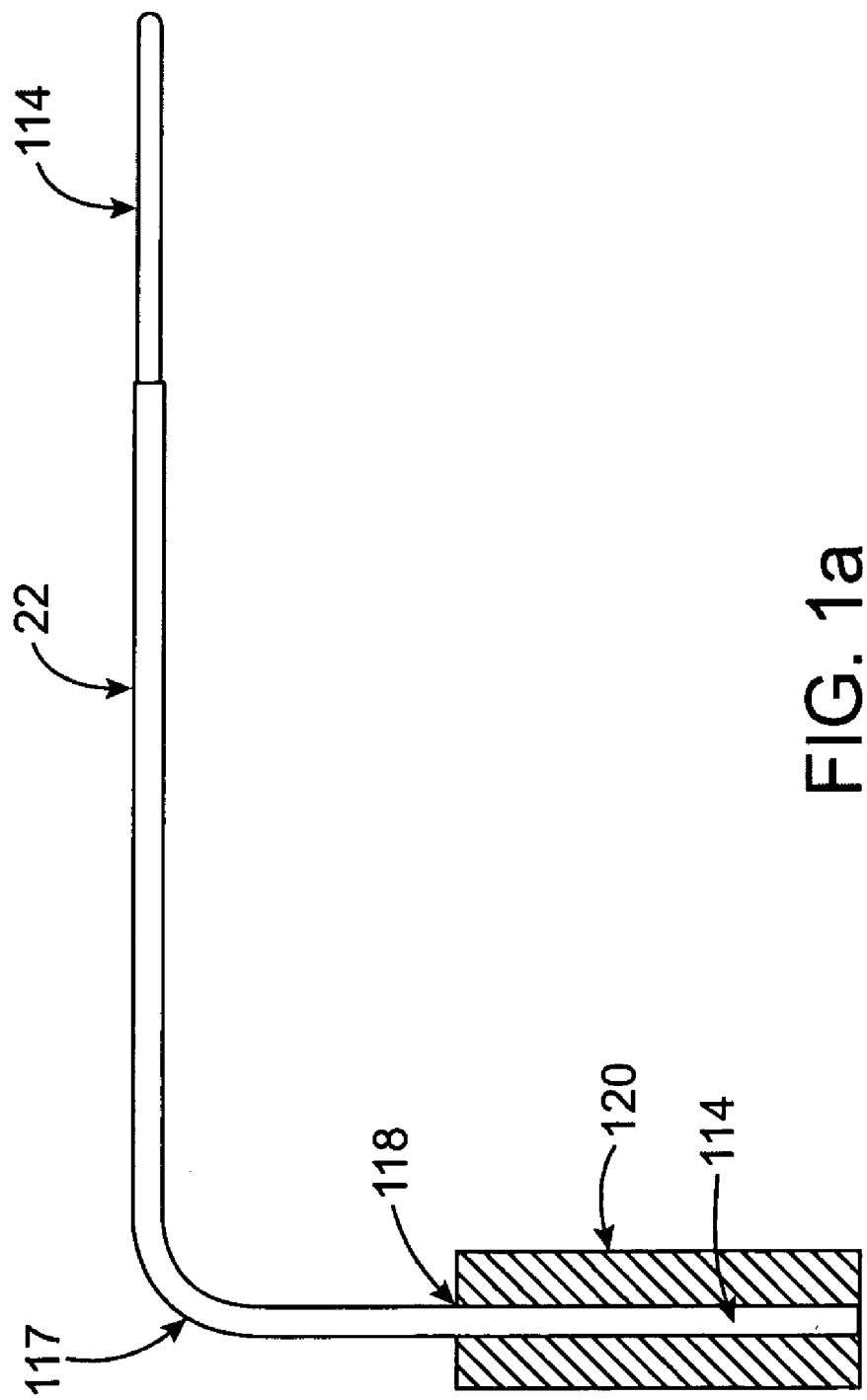

ULTRASOUND CATHETER AND METHODS FOR MAKING AND USING SAME

CROSS-REFERENCES TO RELATED APPLICATIONS

This application is related to pending U.S. patent application Ser. No. 10/229,371, entitled "Ultrasound Catheter for Disrupting Blood Vessel Obstructions," the full disclosure of which is hereby incorporated by reference.

BACKGROUND OF THE INVENTION

The present invention relates generally to medical devices and methods. More specifically, the present invention relates to ultrasound catheter devices, methods for making the devices, and methods for using the devices to disrupt blood vessel occlusions.

Catheters employing various types of ultrasound transmitting members have been successfully used to ablate or otherwise disrupt obstructions in blood vessels. Specifically, ablation of atherosclerotic plaque or thromboembolic obstructions from peripheral blood vessels such as the femoral arteries has been particularly successful. To disrupt occlusions of small blood vessels, such as coronary arteries or peripheral vessels, ultrasound catheters typically have configurations—size, flexibility, shape and the like—which allow for their advancement through the tortuous vasculature of the aortic arch, coronary tree, peripheral vasculature or other similarly narrow vessels.

Typically, an ultrasound catheter transmits energy from an ultrasound transducer through a transducer horn and then a transmission member, such as a wire, to a distal tip or distal head. Ultrasound energy propagates through the transmission member as a sinusoidal wave to cause the distal head to vibrate. Such vibrational energy is typically utilized to ablate or otherwise disrupt vascular obstructions. Various ultrasonic catheter devices have been developed for use in ablating or otherwise removing obstructive material from blood vessels. For example, U.S. Pat. Nos. 5,267,954 and 5,380,274, issued to the inventor of the present invention and hereby incorporated by reference, describe ultrasound catheter devices for removing occlusions. While many ultrasound catheters have been developed, however, improvements are still being pursued.

To effectively reach various sites for treatment of intravascular occlusions, ultrasound catheters often have lengths of about 150 cm or longer. To reach some sites, such as arterial side-branches, it is often necessary to form a bend in the ultrasound catheter. Such bends are often crudely made in an operating room, vascular suite or other setting by a surgeon, cardiologist, interventional radiologist or other physician manually bending the catheter with pliers, surgical forceps or some other instrument. This technique has several drawbacks. First, it is inaccurate and does not always result in a bend at a desired location along the catheter or in a bend having a desired angle. Second, because the user bends the catheter when the catheter is already assembled, with the transmission member already in place, a strain is placed on the transmission member by the bending process. The transmission member is typically bent to as acute of an angle as the catheter body is bent, and the bending process itself stresses the transmission member. Even slight stresses placed on the transmission member by such a bending procedure may cause the transmission member to break prematurely, leading to a reduced usable life for the ultrasound catheter. This susceptibility for premature breakage is compounded by the fact that currently available ultrasonic transmission wires typically break toward their distal ends, where the cross-sectional areas of the wires become smaller.

Therefore, a need exists for ultrasound catheter devices and methods for making and using such devices that include at least one bend for enhancing positioning and/or advancement of the catheter in a blood vessel. Ideally, such catheter devices would be durable enough to last longer than a conventional ultrasound catheter that is hand-bent by a surgeon or other user immediately before use. Ultrasound catheters may also benefit from additional improvements, such as over-the-wire configurations, improved configurations of a distal head of the catheter, catheters that allow for various modes of operation, catheters with enhanced lubricity and the like. At least some of these objectives will be met by the present invention.

BRIEF SUMMARY OF THE INVENTION

Ultrasound catheter devices and methods of the present invention provide enhanced disruption of blood vessel obstructions. Generally, ultrasound catheters include an elongate flexible catheter body with at least one lumen, an ultrasound transmission member extending longitudinally through the lumen and, in many embodiments, a guidewire tube extending through the lumen. A distal head for disrupting occlusions is coupled with the distal end of the ultrasound transmission member and is positioned adjacent the distal end of the catheter body. Various embodiments include novel features such as a bend in the catheter body to facilitate positioning and/or advancement of the catheter, over-the-wire configurations, improved configurations of a distal head of the catheter, catheters that allow for various modes of operation, catheters with enhanced lubricity and the like. Methods for making ultrasound catheters may include methods for making a bend in the catheter, methods for sterilizing a catheter using electron-beam radiation and/or the like.

In one aspect of the invention, an ultrasound catheter for disrupting occlusions in blood vessels comprises an elongate flexible catheter body having a proximal end, a distal end, at least one lumen, and at least one bend in the catheter body nearer the distal end than the proximal end. The catheter also includes an ultrasound transmission member extending longitudinally through the lumen of the catheter body, the ultrasound transmission member having a proximal end connectable to a separate ultrasound generating device and a distal end disposed adjacent the distal end of the catheter body. Finally, the catheter includes a distal head coupled with the distal end of the ultrasound transmission member, the distal head positioned adjacent the distal end of the catheter body.

Generally, the bend in the catheter may be placed in any desired location and have any desired angle, relative to the longitudinal axis of the catheter body. In some embodiments, for example, the bend in the catheter body is disposed along the catheter body at a location between 5 mm and 30 mm from the distal end. In some embodiments, the bend in the catheter body has an angle of less than 90 degrees. For example, the bend may have an angle of between 20 degrees and 50 degrees in some embodiments. In some embodiments, the bend in the catheter body causes a corresponding bend in the ultrasound transmission member. In this case, sometimes the bend in the catheter body has an angle greater than a corresponding angle of the corresponding bend in the ultrasound transmission member. Optionally, the catheter may further include a sheath disposed over at least a portion of the distal end of the catheter body for maintaining the bend in the catheter body. For example, the sheath may be disposed over the portion of the distal end during non-use of the catheter and is removed from the catheter body before use. In some embodiments, the catheter may further include a hydrophilic coating disposed along an outside surface of at least a portion of the catheter body. The hydrophilic coating may be any suitable coating.

The distal head of the catheter device may have any of a number of different configurations and features. For example, in some embodiments the distal head is not directly affixed to the distal end of the catheter body. Some embodiments further include at least one side-opening through a side of the distal head. The side-opening may comprise, for example, a space for introducing an adhesive to couple the distal head with a guidewire tube disposed in the lumen of the catheter body. Optionally, the side-opening may extend around at least a portion of a circumference of the distal head. For example, the side-opening may take the form of a slot.

Some embodiments of the ultrasound catheter include a guidewire tube having a proximal end and a distal end and extending longitudinally through at least a portion of the lumen of the catheter body and through at least a portion of the distal head. The guidewire tube may comprise any suitable material such as, in some embodiments, a polyimide material. In some embodiments, the guidewire tube is affixed to the distal head. Furthermore, the guidewire tube may also be affixed to the catheter body. The side-opening in the distal head, as just described, may sometimes be used for introducing adhesive to affix the distal head to a guidewire tube. For example, the catheter may include a side-opening in the distal head and a polymer sleeve disposed around a portion of the distal head, the polymer sleeve being coupled with the guidewire tube by adhesive extending through the side-opening.

A guidewire tube of an ultrasound catheter may be an over-the-wire tube, a rapid-exchange tube, a monorail tube or any other suitable guidewire tube. In some embodiments, for example, the proximal end of the guidewire tube exits the catheter body nearer the proximal end of the catheter body than the distal end of the catheter body. Alternatively, the guidewire tube may exit the catheter body nearer the distal end of the catheter body than the proximal end of the catheter body. In still other embodiments, the proximal end of the guidewire tube exits the catheter body through the proximal end of the catheter body. The last of these embodiments may further include a connector device coupled with the proximal end of the catheter body and the proximal end of the guidewire tube, wherein the guidewire tube extends through at least a portion the connector device. Such a catheter may further comprise a coupling member, such as a sheath or sleeve, for coupling the connector device with the catheter body. In other embodiments, the guidewire tube may exit the catheter body through a guidewire port positioned along the catheter body at a location separate from the connector device. Such a guidewire port may sometimes include a flexible extension. In some embodiments, the guidewire tube may include micro-perforations or apertures along all or a portion of its length. The micro-perforations may allow, for example, passage of fluid into the guidewire lumen to provided lubrication to a guidewire.

In some embodiments, the connector device just described includes a distal portion for coupling with the proximal end of the catheter body, the distal portion having a common lumen. The device further includes a proximal ultrasound transmission arm having an ultrasound transmission lumen in communication with the common lumen and a proximal guidewire arm having a guidewire lumen in communication with the common lumen. Optionally, the connector device may also include a proximal infusion arm having an infusion port in communication with the common lumen. In some embodiments, the ultrasound transmission arm, the distal portion, and the catheter body are disposed along a common longitudinal axis. In some embodiments, the guidewire arm branches from the distal portion of the connector at less of an angle than the infusion arm branches from the distal portion of the connector. Any such embodiments may further include a coupling member for coupling the distal portion of the connector device with the catheter body.

In some embodiments of the catheter, the ultrasound transmission member may transmit ultrasound energy from the separate ultrasound device as both pulsed energy and continuous energy. Such embodiments may optionally include an actuator coupled with the ultrasound generating device for switching between transmission of the pulsed energy and transmission of the continuous energy to the ultrasound transmission member. Any of the above embodiments may be sterilized by exposure to an electron beam.

In another aspect, an ultrasound catheter for disrupting occlusions in blood vessels comprises: an elongate flexible catheter body having a proximal end, a distal end, at least one lumen extending longitudinally through the body; an ultrasound transmission member extending longitudinally through the lumen of the catheter body, the ultrasound transmission member having a proximal end connectable to a separate ultrasound generating device and a distal end disposed adjacent the distal end of the catheter body; and a distal head coupled with the distal end of the ultrasound transmission member, the distal head positioned adjacent the distal end of the catheter body; wherein the ultrasound transmission member transmits at least two different types of ultrasound energy from the separate ultrasound generator. In some embodiments, the catheter may further include at least one bend in the catheter body near the distal end. Optionally, the separate ultrasound generating device may include an actuator for switching between transmitting a first type of ultrasound energy to the ultrasound transmission member and transmitting at least a second type of ultrasound energy to the ultrasound transmission member. For example, the first type of ultrasound energy may comprise pulsed ultrasound energy and the second type of ultrasound energy may comprise continuous ultrasound energy.

In another aspect, an ultrasound catheter for disrupting occlusions in blood vessels includes an elongate flexible catheter body having a proximal end, a distal end, an external surface, an internal surface, at least one lumen, and a hydrophilic coating disposed along at least a portion of the external surface. The catheter also includes an ultrasound transmission member extending longitudinally through the lumen of the catheter body, the ultrasound transmission member having a proximal end connectable to a separate ultrasound generating device and a distal end disposed adjacent the distal end of the catheter body. Finally, the catheter includes a distal head coupled with the distal end of the ultrasound transmission member, the distal head positioned adjacent the distal end of the catheter body. In some embodiments, the catheter further comprises at least one bend in the catheter body.

In another aspect, an ultrasound catheter for disrupting occlusions in blood vessels comprises: an elongate flexible catheter body having a proximal end, a distal end, at least one lumen extending longitudinally through the body; an ultrasound transmission member extending longitudinally through the lumen of the catheter body, the ultrasound transmission member having a proximal end connectable to a separate ultrasound generating device and a distal end disposed adjacent the distal end of the catheter body; and a distal head coupled with the distal end of the ultrasound transmission member, the distal head positioned adjacent the distal end of the catheter body, wherein the ultrasound catheter is sterilized by exposure to an electron beam. Some embodiments of such catheters may further include a bend in the catheter body near the distal end.

In another aspect, an improved ultrasound catheter of the type comprising an elongate flexible catheter body having a proximal end, a distal end, and at least one lumen, an ultrasound transmission member extending longitudinally through the lumen of the catheter body, and a distal head coupled with a distal end of the ultrasound transmission member, includes an improvement comprising at least one bend in the catheter body nearer the distal end of the catheter body than the proximal end.

In still another aspect, an improved ultrasound catheter of the type comprising an elongate flexible catheter body having a proximal end, a distal end, and at least one lumen, an ultrasound transmission member extending longitudinally through the lumen of the catheter body, and a distal head coupled with a distal end of the ultrasound transmission member, includes an improvement comprising a hydrophilic coating disposed along at least a portion of an external surface of the catheter body.

In another aspect, an ultrasound system for disrupting occlusions in blood vessels comprises an ultrasound catheter, which includes: an elongate flexible catheter body having a proximal end, a distal end, at least one lumen, and at least one bend in the catheter body nearer the distal end than the proximal end; an ultrasound transmission member extending longitudinally through the lumen of the catheter body, the ultrasound transmission member having a proximal end and a distal; and a distal head coupled with the distal end of the ultrasound transmission member, the distal head positioned adjacent the distal end of the catheter body. The ultrasound system also includes a separate ultrasound generating device coupled with the proximal end of the ultrasound transmission member.

In some embodiments, the separate ultrasound generating device includes an actuator for switching between transmitting a first type of ultrasound energy to the ultrasound transmission member and transmitting at least a second type of ultrasound energy to the ultrasound transmission member. For example, in some embodiments the first type of ultrasound energy comprises pulsed ultrasound energy and the second type of ultrasound energy comprises continuous ultrasound energy.

In yet another aspect, a method of making an ultrasound catheter for disrupting occlusions in blood vessels comprises forming a catheter body over a mandrel, wherein the mandrel includes at least one bend for forming a corresponding bend in the catheter body; separating the catheter body from the mandrel. The method then involves inserting an ultrasound transmission member into a lumen of the catheter body, wherein inserting the ultrasound transmission member reduces an angle of the at least one bend in the catheter body.

Any angles, locations or the like for one or more angle(s) may be used. For example, in one embodiment the method comprises forming the body over a mandrel having a bend of between about 20 degrees and about 90 degrees. In some embodiments, inserting the ultrasound transmission member into the lumen reduces the angle of the bend in the catheter body to between 15 degrees and 80 degrees. Sometimes, inserting the ultrasound transmission member into the lumen causes the ultrasound transmission member to bend at the bend in the catheter body. In some embodiments, for example, the ultrasound transmission member bends at an angle less than the angle of the bend in the catheter body.

Optionally, some embodiments of the method for making the catheter further include placing a sheath over at least a portion of the catheter body to maintain the bend in the catheter body. Also optionally, some embodiments further involve directing an electron beam at the ultrasound catheter to sterilize the catheter.

In still another aspect, a method of making an ultrasound catheter for disrupting occlusions in blood vessels comprises placing a catheter body over a mandrel, wherein the mandrel includes at least one bend for forming a corresponding bend in the catheter body, heating the catheter body, removing the catheter body from the mandrel, and inserting an ultrasound transmission member into a lumen of the catheter body, wherein inserting the ultrasound transmission member reduces an angle of the at least one bend in the catheter body.

In another aspect, a method for disrupting an occlusion in a blood vessel comprises positioning an ultrasound catheter in the blood vessel such that a distal end of the catheter is adjacent the occlusion, transmitting a first type of ultrasound energy to an ultrasound transmission member of the ultrasound catheter to disrupt the occlusion, and transmitting a second type of ultrasound energy to the ultrasound transmission member to further disrupt the occlusion. In some embodiments of the method, the first type of ultrasound energy comprises pulsed energy and the second type of energy comprises continuous energy. In other embodiments, the first type of ultrasound energy comprises continuous energy and the second type of energy comprises pulsed energy. The method may further comprise switching from transmitting the second type of ultrasound energy to transmitting the first type of ultrasound energy. Any of these methods may also include repeating at least one of the transmitting and switching steps at least once.

In some cases, transmitting the first type of energy and transmitting the second type of energy involves activating an actuator on a separate ultrasound generating device coupled with the ultrasound catheter. In some embodiments, positioning the catheter comprises using a bend in the ultrasound catheter to advance the catheter into a position adjacent the occlusion. The method may further comprise using a bend in the catheter to reposition the ultrasound catheter in an additional blood vessel adjacent an additional occlusion and transmitting at least one form of ultrasound energy to the ultrasound transmission member to disrupt the additional occlusion.

In any of the above methods, positioning the device may involve advancing the ultrasound catheter over a guidewire. Such advancing of the ultrasound catheter over the guidewire may involve advancing over a guidewire disposed in a guidewire lumen of the catheter, the guidewire lumen extending at least a majority of a length of the catheter. Optionally, the guidewire lumen may extend the full length of the catheter and may be coupled with a connector device coupled with a proximal end of the ultrasound catheter. In some embodiments, the method may further involve injecting dye into the blood vessel through the guidewire lumen. Alternatively, dye may be injected through a catheter via means other than a guidewire lumen.

BRIEF DESCRIPTION OF THE DRAWING FIGURES

FIG. 1 is a perspective view of a system including an ultrasound catheter device and ultrasound energy source according to an embodiment of the present invention;

FIG. 1a is a side view of a mandrel and a catheter body, showing a method for making a catheter body according to an embodiment of the present invention;

FIG. 2b is a partial cut-away perspective view of an ultrasound transmission member with a friction reducing coating or jacket according to an embodiment of the present invention;

DETAILED DESCRIPTION OF THE INVENTION

Figure 1B:
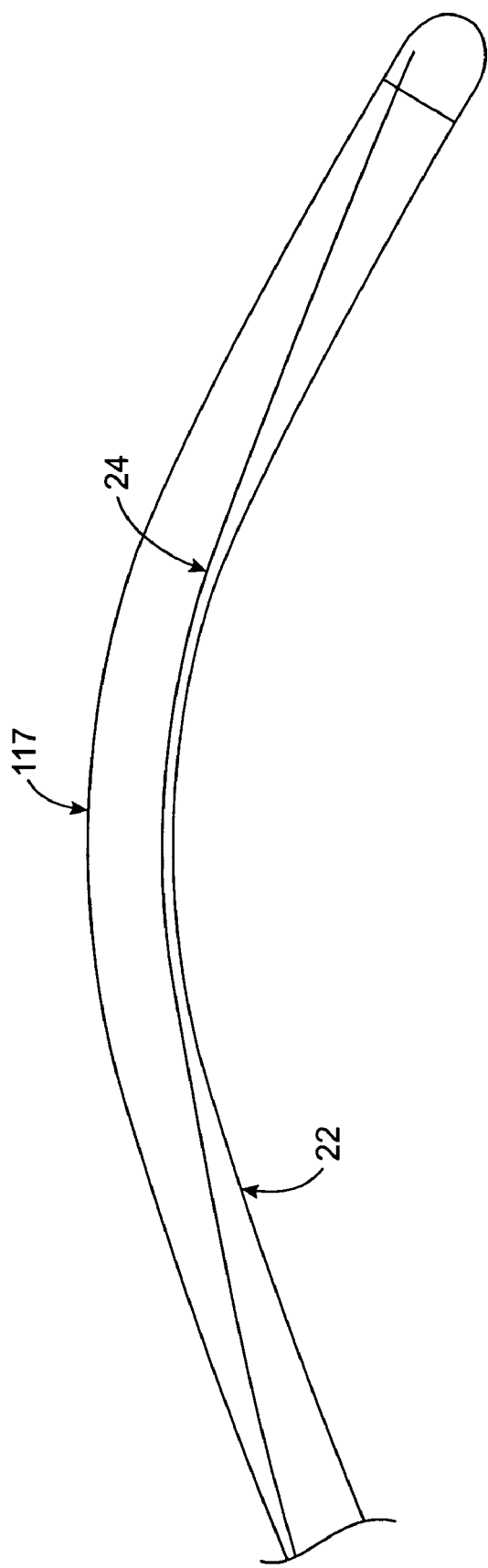
FIG. 1b is a cross-sectional side view of a distal end of a catheter body and an ultrasound transmission member within the body according to an embodiment of the present invention.

Ultrasound catheter devices and methods of the present invention may generally be used for treating occlusions in blood vessels. Catheter devices generally include a catheter body, an ultrasound energy transmission member disposed within the catheter body and a distal head coupled with the energy transmission member and disposed at or near the distal end of the catheter body. The ultrasound transmission member transmits ultrasound energy from an ultrasound transducer to the distal head, causing the head to vibrate and, thus, disrupt vascular occlusions.

Some embodiments of an ultrasound catheter include at least one bend in the catheter body for enhancing positioning and/or advancement of the catheter in a blood vessel. A bend may facilitate, for example, placement or repositioning of the catheter in a branching vessel that branches off of a larger vessel. The bend in the catheter body is typically formed by heating the body while it is on a mandrel, but other suitable methods may be employed. The bend is formed when before the ultrasound transmission member is inserted into the catheter body, so as to reduce stress on the transmission member.

In some embodiments, the transmission member bends somewhat when it is placed in the catheter body, but to a lesser degree than the catheter body is bent. Various locations for one or more bends n the catheter body, various angles for the bend(s) and the like may be used in various embodiments of the ultrasound catheter, as desired.

Other embodiments of an ultrasound catheter may include various other improvements. For example, some embodiments include a sheath for maintaining a bend in the catheter when not in use. Some embodiments include a hydrophilic coating disposed over at least a portion of the external surface of the catheter body to enhance the lubricity of the body and facilitate advancement of the catheter through a blood vessel. Some embodiments include an over-the-wire guidewire tube to allow for enhanced injection of dye or other fluids near an occlusion and/or to facilitate guidewire changing during a procedure. Some embodiments include a distal head with an opening configured for enhanced attachment of the head to a guidewire tube disposed within the catheter body. In some embodiments, an ultrasound transducer coupled with the ultrasound catheter may be switched, via an actuator, between a pulsed ultrasound energy mode, a continuous ultrasound energy mode and/or other ultrasound energy modes, as desired. Some embodiments are sterilized via electron-beam sterilization. In any given embodiment, an ultrasound catheter may include any suitable combination of the features described above, as well as any other suitable features. These features will be described in further detail below in the form of examples, but these examples should in no way be interpreted to limit the scope of the invention as it is defined in the claims.

Referring now to FIG. 1, one embodiment of an ultrasound catheter system 20 suitably includes an ultrasound catheter 10, a proximal end connector assembly 12 coupled with catheter 10, an ultrasound transducer 14 coupled with the proximal end of a proximal connector assembly 12, and an ultrasound generator 16 with a power cord 17 and foot-actuated on/off switch 18, which is operatively coupled with ultrasound transducer 14 to provide ultrasonic energy to transducer 14 and, thus, to ultrasound catheter 10. Generally, catheter 10 includes an ultrasound transmission member, or wire (not shown), for transmitting energy from the transducer 14 to a distal head 26 of the catheter. In some embodiments, catheter 10 includes one or more bends 117 along its length for facilitating positioning and/or advancement of catheter 10. Components of system 20 may be coupled via any suitable means, such as connecting wires 11a, 11b of any kind, wireless connections or the like.

Proximal connector assembly 12, described more fully below, may have a connector device 15, such as the W-connector that is shown, a Y-connector or the like. Connector device 15 may include any suitable number of side-arms or ports, such as a guidewire arm 19 for passage of a guidewire and an infusion arm 13 for infusing and/or withdrawing irrigation fluid, dye and/or the like. In other embodiments, catheter 10 may be passed along a guidewire which accesses catheter 10 via a side aperture rather than connector device 15. For example, some embodiments include a rapid exchange guidewire lumen. Ultrasound catheters 10 of the present invention may be used with any suitable proximal devices, such as any suitable ultrasound transducer 14, ultrasound generator 16, connector assembly 12, connector device(s) 15 and/or the like. Therefore, exemplary FIG. 1 and any following descriptions of proximal apparatus or systems for use with ultrasound catheters 10 should not be interpreted to limit the scope of the present invention as defined in the appended claims.

In some embodiments, ultrasound generator 16, ultrasound transducer 14 or any other suitable component of system 20 may include one or more actuators 119 for switching between two or more modes or types of ultrasound energy transmission to an ultrasound transmission member of catheter 10. Actuator 119 may be used, for example, to switch between transmission of pulsed ultrasound signal and continuous ultrasound signal. Providing two or more different types of ultrasound signal may enhance disruption of a vascular occlusion, and in various embodiments, switching between types of signals may be performed in any order desired, as many times as desired, without stopping the transmission of ultrasound energy to make the switch and/or the like. Although actuator 119 is pictured on ultrasound generator 16 in FIG. 1, it may be given any other location and configuration.

Figure 2A:
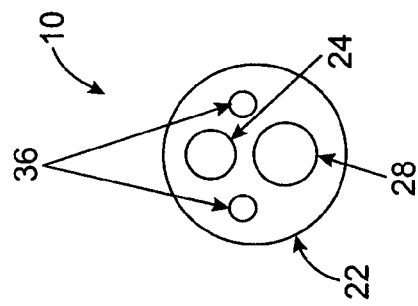
FIG. 2a is a cross-sectional front view of an ultrasound catheter device from the perspective of the arrows labeled "a" in FIG. 2.
Figure 2:
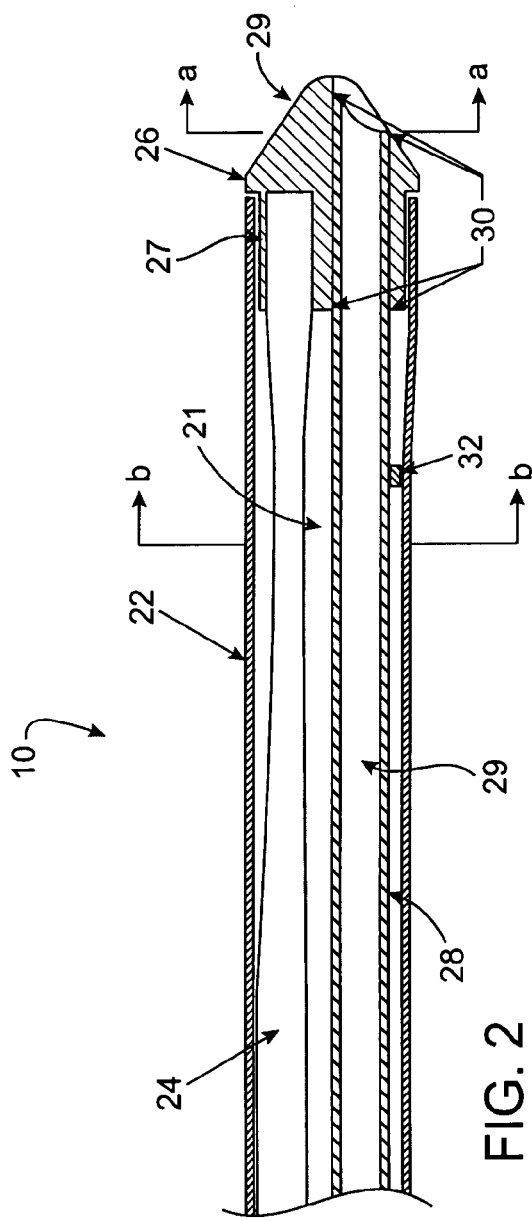
FIG. 2 is a cross-sectional side view of a distal end of an ultrasound catheter device according to an embodiment of the present invention.

Referring now to FIG. 2, a cross-sectional side view of the distal end of one embodiment of ultrasound catheter 10 is shown. Generally, ultrasound catheter 10 suitably includes an elongate catheter body 22 with at least one hollow catheter body lumen 21. In FIG. 2, catheter body 22 is shown having one lumen, but it may have any number of lumens in various embodiments. Disposed longitudinally within catheter body lumen 21 are an ultrasound transmission member 24 and a hollow guidewire tube 28 forming a guidewire lumen 29. Coupled with the distal ends of ultrasound transmission member 24 and guidewire tube 28 is a distal head 26, positioned adjacent the distal end of catheter body 22.

Generally, the various coupled components described above may be coupled by any suitable means, such as adhesives, complementary threaded members, pressure fittings, and the like. For example, distal head 26 may be coupled with ultrasound transmission member 24 and guidewire tube 28 with any suitable adhesive substance. In one embodiment, for example, guidewire tube 28 is coupled with distal head 26 by means of adhesive at multiple head/guide wire adhesive points 30. In some embodiments, guidewire tube 28 may also be coupled with catheter body 22 by adhesive or other means at one or more body/guidewire adhesive points 32. As explained further below, some embodiments of distal head 26 include one or more apertures for facilitating introduction of adhesive to couple distal head 26 to guidewire tube 28.

Catheter body 22 is generally a flexible, tubular, elongate member, having any suitable diameter and length for reaching a vascular occlusion for treatment. In one embodiment, for example, catheter body 22 preferably has an outer diameter of between about 0.5 mm and about 5.0 mm. In other embodiments, as in catheters intended for use in relatively small vessels, catheter body 22 may have an outer diameter of between about 0.25 mm and about 2.5 mm. Catheter body 22 may also have any suitable length. Some ultrasound catheters, for example, have a length in the range of about 150 cm. However, any other suitable length may be used without departing from the scope of the present invention. Examples of catheter bodies similar to those which may be used in the present invention are described in U.S. Pat. Nos. 5,267,954 and 5,989,208, which were previously incorporated herein by reference.

As mentioned above, and with reference again to FIG. 1, in some embodiments of ultrasound catheter 10 catheter body 22 includes one or more bends 117 along its length, for enhancing advancing and/or positioning catheter 10. For example, bend 117 may facilitate advancement of catheter 10 into a side-branch vessel of a larger vessel. Bend 117 may be located at any suitable location along catheter 10 and may have any suitable angle, relative to the longitudinal axis of catheter 10, and any number of bends 117 having any number of configurations are contemplated within the scope of the invention. In some embodiments, for example, catheter body 22 includes one bend, located between about 1 mm and about 20 mm from the distal end of catheter body 22, and preferably between about 5 mm and about 15 mm from the distal end of catheter body 22, and even more preferably between about 7 mm and about 10 mm from the distal end of catheter body 22.

Generally, and with reference now to FIG. 1a, in one embodiment of a method for making catheter 10, bend 117 in catheter body 22 is formed by positioning catheter body 22 on a mandrel 114. In some embodiments, catheter body 22 is formed on mandrel 114, while in other embodiments catheter body 22 may be preformed and then placed on mandrel 114 for forming bend 117. In either case, mandrel 114 may include or be coupled with a stopper member 120. Stopper member 120 generally maintains a position of catheter body 22 on mandrel 114, to help ensure the formation of bend 117 in a desired location. In some embodiments, catheter body 22 or material for making catheter body 22 is placed on mandrel 114 and is advanced until one end 118 of the material is stopped by stopper 120. In some embodiments, catheter body 22 is then heated in order to form bend 117. After bend 117 is formed, catheter body 22 may be separated from mandrel 114 and used as part of catheter 10. This is but one example of a method for making catheter body 22, and any suitable alternative methods including a mandrel for making a bend are contemplated within the scope of the invention.

As previously mentioned, bend 117 may have any suitable angle of deflection, relative to the longitudinal axis of catheter 10. In some embodiments, for example, bend 117 may have an angle of between about 20 degrees and about 50 degrees, and preferably an angle of between about 30 degrees and about 40 degrees. In some embodiments, catheter body 22 may be formed having an angle that is greater, or more severe, than the final angle of bend 117 of catheter 10. In other words, when an ultrasound transmission member is inserted into a bent catheter body 22, the ultrasound transmission member will typically bend slightly to conform to bend 117, and catheter body 22 will straighten slightly to conform to the ultrasound transmission member. Thus, catheter body 22 in some embodiments will be formed having bend 117 with an angle that is larger than the final angle that bend 117 will have when the ultrasound transmission member is inserted. In FIG. 1a, for example, bend 117 has an angle of approximately 90 degrees. Other embodiments may use any other suitable angles for bend 117 of catheter body 22 to arrive at a desired angle for bend 117 when the ultrasound transmission member is inserted. For example, mandrels may have bends with angles of between about 20 degrees and about 90 degrees, or any other suitable angle, and may result in a catheter body having a bend of between about 15 degrees and about 80 degrees when an ultrasound transmission wire is inserted, or any other suitable angle.

As just discussed, in one aspect of the invention, and with reference now to FIG. 1b, bend 117 in catheter body 22 has a more acute angle than a corresponding bend in ultrasound transmission member 24 inserted in catheter body 22. This generally occurs because catheter body 22 straightens somewhat when ultrasound transmission member 24 is inserted and ultrasound transmission member 24 bends somewhat to conform to bend 117 in catheter body 22. In some embodiments, as shown, ultrasound transmission member 24 is at least partially free to move within the lumen of catheter body 22 so that it remains as straight as possible and is not forced to bend to the same extent that catheter body 22 is bent. This less-bent configuration places less of a strain on ultrasound transmission member 24 during use, which in turn results in less wear and tear of ultrasound transmission member 24 and a longer life of the device than would occur if ultrasound transmission member 24 were more severely bent.

Because ultrasound transmission member 24 may tend to straighten bend 117 to a degree, some embodiments of catheter 10 include a sheath, sleeve, cover or other shape-retention device for placement over at least a portion of catheter body 22 when catheter 10 is not in use. For example, a shape-retention device may comprise a short, rigid, plastic sheath, having a bend in its length. When placed over catheter body 22 at bend 117, the sheath may help retain the shape and angle of bend 117 during non-use. When catheter 10 is to be used, the sheath is removed. Any suitable size, shape or material may be used for making such a shape-retention device and any such device falls within the scope of the present invention.

In some embodiments, catheter 10 includes a coating on the external or outward-facing surface of catheter body 22. Coatings may alternatively be applied to any other surface or combination of surfaces of catheter 10, as desired. A coating may be made of any suitable material, may have any suitable thickness and may cover any suitable length of catheter body 22. In some embodiments, for example, the coating is made from one or more hydrophilic materials, which provide increased lubricity and decreased friction for the external surface of catheter body 22, thus enhancing advancement and/or positioning of catheter 10 in a blood vessel. For example, a hydrophilic coating on catheter body 22 may be similar to the coatings described in U.S. Pat. No. 5,538,512, entitled "Lubricious Flow Directed Catheter," the full disclosure of which is hereby incorporated by reference. As described in U.S. Pat. No. 5,538,512, materials used for coatings may include, but are not limited to, polymers or oligomers of monomers selected from ethylene oxide and its higher homologs, including up to 6 carbon atoms; 2-vinyl pyridine; N-vinylpyrrolidone; polyethylene glycol acrylates such as mono-alkoxy polyethylene glycol mono(meth) acrylates, including mono-methoxy triethylene glycol mono (meth) acrylate, mono-methoxy tetraethylene glycol mono (meth) acrylate, polyethylene glycol mono (meth) acrylate; other hydrophilic acrylates such as 2-hydroxyethylmethacrylate, glycerylmethacrylate; acrylic acid and its salts; acrylamide and acrylonitrile; acrylamidomethylpropane sulfonic acid and its salts, cellulose, cellulose derivatives such as methyl cellulose ethyl cellulose, carboxymethyl cellulose, cyanoethyl cellulose, cellulose acetate, polysaccharides such as amylose, pectin, amylopectin, alginic acid, and cross-linked heparin; maleic anhydride; aldehydes; etc. These monomers may be formed into homopolymers or block or random copolymers. The use of oligomers of these monomers in coating the catheter for further polymerization is also an alternative. Preferred monomers include ethylene oxide; 2-vinyl pyridine; N-vinylpyrrolidone and acrylic acid and its salts; acrylamide and acrylonitrile each polymerized (with or without substantial crosslinking) into homopolymers, or into random or block copolymers.

Additionally, hydrophobic monomers may be included in the polymeric coating material in an amount up to about 30% by weight of the resulting copolymer, so long as the hydrophilic nature of the resulting copolymer is not substantially compromised. Suitable monomers include ethylene, propylene, styrene, styrene derivatives, alkylmethacrylates, vinylchloride, vinylidenechloride, methacrylonitrile, and vinyl acetate. Preferred, because of their propensity for ease of linkage to the typical polymeric catheter substrates, are ethylene, propylene, styrene, and styrene derivatives.

For further details regarding materials for coatings, methods for preparing and/or applying coatings, and/or the like, reference may be made to U.S. Pat. No. 5,538,512. Alternatively, any other suitable hydrophilic coating may be applied to an exterior surface and/or any other surface of catheter 10, without departing from the scope of the present invention.

Returning to FIG. 2, in many embodiments, ultrasound transmission member 24 extends longitudinally through catheter body lumen 21 to transmit ultrasonic energy from ultrasound transducer 14, connected to the proximal end of catheter 10, to the distal end of catheter 10. Ultrasound transmission member 24 may be formed of any material capable of effectively transmitting ultrasonic energy from ultrasound transducer 14 to the distal end of catheter body 22, including but not limited to metals such as titanium and nickel alloys.

In accordance with one aspect of the invention, all or a portion of ultrasound transmission member 24 may be formed of one or more materials which exhibit superelastic properties. Such material(s) should preferably exhibit superelasticity consistently within the range of temperatures normally encountered by ultrasound transmission member 24 during operation of ultrasound catheter apparatus 10. Specifically, all or part of the ultrasound transmission member 24 may be formed of one or more metal alloys known as "shape memory alloys."

Use of supereleastic metal alloys in ultrasound transmission members is described in U.S. Pat. No. 5,267,954, previously incorporated by reference. Examples of superelastic metal alloys which may be used are described in detail in U.S. Pat. Nos. 4,665,906 (Jervis); 4,565,589 (Harrison); 4,505,767 (Quin); and 4,337,090 (Harrison), the entire disclosures of which are hereby incorporated by reference insofar as they describe the compositions, properties, chemistries and behavior of specific metal alloys which are superelastic within the temperature range at which ultrasound transmission member 24 of the present invention operates, any and all of which superelastic metal alloys may be used to form ultrasound transmission member 24 of the present invention.

In many embodiments, ultrasound transmission member 24 includes one or more tapered regions along a portion of its length, towards its distal end. Such a tapered region 23 decreases the distal rigidity of ultrasound transmission member 24, thus amplifying ultrasound energy transmitted along ultrasound transmission member 24 to distal head 26. Tapered region 23 typically divides the transmission member 24 between a proximal portion and a distal portion, which both typically have a larger cross-sectional diameter than tapered region 23, as pictured in FIG. 2. A thicker distal portion, for example, may enhance stability of the connection between ultrasound transmission member 24 and distal head 26. Other embodiments are contemplated, however. For example, tapered region 23 may be positioned at the extreme distal end of transmission member 24. In still other embodiments, ultrasound transmission member 24 may include multiple tapered portions, widened portions and/or the like. Thus, ultrasound transmission member 24 may be configured with any suitable length, combinations of diameters and tapers, or any other suitable shapes, sizes or configurations to advantageously transmit ultrasound energy from transducer 14 to distal tip 26.

With reference now to FIG. 2b, in some embodiments ultrasound transmission member 24 may include a low-friction coating 25, jacket or similar covering on all or a portion of its outer surface. Coating 25 may be disposed on the outer surface of ultrasound transmission member 24 so as to completely cover ultrasound transmission member 24 along its entire length, or along a discrete region or regions thereof.

Such coating or jacket 25 may comprise a layer of low friction polymer material such as polytetrafluoroethylene (PTFE), TEFLON™ (available from Dupont, Inc., Wilmington, Del.) or other plastic materials such as polyethylene. Coating 25 may be applied as a liquid and subsequently allowed to cure or harden on the surface of ultrasound transmission member 24. Alternatively, coating 25 may be in the form of an elongate tube, disposable over the outer surface of ultrasound transmission member 24. Generally, coating 25 serves to prevent or diminish friction between the outer surface of ultrasound transmission member 24 and the adjacent structures of catheter 10 or proximal end connector assembly 12 through which ultrasound transmission member 24 extends.

In most embodiments, distal head 26 is mounted on or otherwise coupled with the distal end of ultrasound transmission member 24. In many embodiments, as shown in FIG. 2, distal tip includes a proximal region 27 with an outer diameter configured to fit within the distal end of catheter body lumen 21 and a distal region 29 with a slightly larger diameter than proximal region 27. In many embodiments, all or a portion of distal region 29 of distal head 26 will have an outer diameter approximately the same as the outer diameter of catheter body 22. Thus, in embodiments like the one pictured in FIG. 2, the distal end of catheter body 22 overlaps at least a portion of distal head 26. The amount of overlap may vary in different embodiments, so that in some embodiments catheter body 22 may completely overlap distal head 26. This overlapping may enhance stability of the distal end of catheter 10 and distal head 26 in particular.

Figure 3:
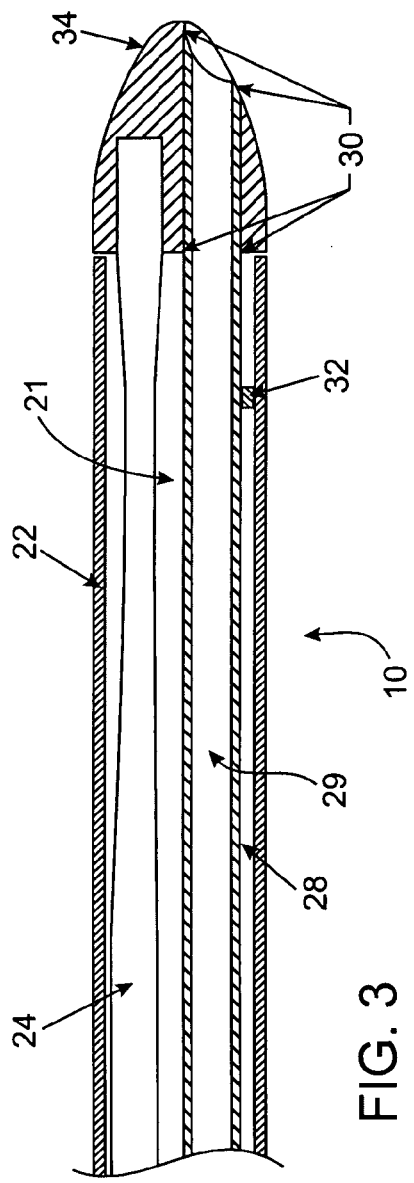
FIG. 3 is a cross-sectional view of a distal end of an ultrasound catheter device according to another embodiment of the present invention.

In another embodiment, as shown in FIG. 3, distal head 34 is configured so that its proximal end abuts the distal end of catheter body 22. In this embodiment, distal head 26 is held in position adjacent catheter body 22 by its attachment to ultrasound transmission member 24 and/or guide wire tube 28 and does not fit within catheter body lumen 21. Typically, in such an embodiment, all or a portion of distal head 34 will have an outer diameter that is approximately equal in dimension to the outer diameter of catheter body 22.

As is evident from distal heads 26 and 34, shown in FIGS. 2 and 3, distal heads may have any suitable configuration, shape, and size suitable for ablating or otherwise disrupting occlusions. For example, distal head 26, 34 may have a shape that is bulbous, conical, cylindrical, circular, rectangular or the like. Similarly, distal head 26, 34 may have dimensions which allow it to fit wholly or partially within the distal end of catheter body lumen 21 or may, alternatively, be disposed completely outside catheter body lumen 21. Thus, the configuration of distal head 26 may take any suitable form and should in no way be limited by the exemplary embodiments pictured in FIGS. 2 and 3 and described above or below.

In some embodiments, distal head 26 is not directly affixed to the distal end of catheter body 22. Instead, in various embodiments, it is held in place by its attachment to either ultrasound transmission member 24, guidewire tube 28, or both. In some embodiments, distal head 26 may additionally be secured to the distal end of catheter body 22 by fitting partially or wholly within catheter body lumen 21, as described above. In embodiments where distal head 26 is not directly affixed to the distal end of catheter body, distal head 26 will be able to move freely, relative to the distal end of catheter body 22. Positioning distal head 26 in this way, without affixing it to catheter body 22, allows greater freedom of movement of head 26, providing enhanced efficiency of ultrasound energy transmission and reduced stress to ultrasound transmission member 24.

Distal head 26 may be coupled indirectly with catheter body 22 at one or more points proximal to the distal end of catheter body 22. In some embodiments, for example, distal head 26 is indirectly coupled to the catheter body 22 via guidewire tube 28, as described further below. For example, distal head 26 may be coupled with guidewire tube 28, and guidewire tube 28 may be coupled with catheter body 22 at a location within 1 cm of the distal end of catheter body 22, at a location around 25 cm from the distal end of catheter body 22, or at any other location or combination of locations. In other embodiments, distal head 26 may be coupled with ultrasound transmission member 24, and ultrasound transmission member 24 may be coupled with catheter body 22 near its proximal end and/or at any other suitable location.

In some embodiments, distal head 26 is formed of radiodense material so as to be easily discernable by radiographic means. For example, distal head 26 may be formed of a metal or metal alloy. Alternatively, distal head 26 may be made of a polymer or ceramic material having one or more radiodense markers affixed to or located within distal head 26. In one embodiment, for example, distal head 26 may be molded of plastic such as acrylonitrile-butadiene-styrene (ABS) and one or more metallic foil strips or other radiopaque markers may be affixed to such plastic distal head 26 in order to impart sufficient radiodensity to permit distal head 26 to be readily located by radiographic means. Additionally, in embodiments wherein distal tip 26 is formed of molded plastic or other non-metallic material, a quantity of radiodense filler such as powdered bismuth or $BaSO_4$ may be disposed within the plastic or other non-metallic material of which distal head 26 is formed so as to impart enhanced radiodensity to distal head 26.

In some embodiments, guidewire tube 28 is also disposed longitudinally within catheter body lumen 21, along all or a portion of the luminal length. Guidewire tube 28 may also extend through distal head 26, as shown in FIGS. 2 and 3, to allow a guidewire to pass through the distal end of distal head 26. Alternatively, guidewire tube 28 and guidewire lumen 29 may be given any suitable configuration, length, diameter and the like suitable for passing catheter 10 along a guide wire to a location for treatment. For example, in some embodiments, a relatively short guidewire lumen 29 may be formed near the distal end of catheter body 22 to permit rapid exchange of catheters. In other embodiments, catheter 10 may include an over-the-wire guidewire tube 28 and guidewire lumen 29 that extend along all or almost all of the length of catheter 10. Such an over-the-wire configuration may be beneficial for providing means for a super-selective dye injection at a location near an occlusion, for facilitating one or more changes of guidewires during a procedure, for enhancing manipulation of catheter 10 and/or the like. In some embodiments, guidewire tube 28 may include micro-perforations or apertures along all or a portion of its length. The micro-perforations may allow, for example, passage of fluid into the guidewire lumen to provided lubrication to a guidewire. In some embodiments having over-the-wire guidewire tubes 28, guidewire lumens 29 may be accessed via a guidewire arm 19 on connector device 15. Again, connector device 15 may comprise a W-connector, a Y-connector or any other suitable device. Thus, catheters 10 of the present invention are not limited to those including guidewire tubes 28 and or guidewire lumens 29 as described by FIGS. 2 and 3, but may include any suitable guidewire lumens, tubes or the like.

In some embodiments, guidewire tube 28 is attached to both distal head 26 and catheter body 22. As previously described, such attachment may be accomplished by any suitable means, such as by an adhesive substance. Generally, guidewire tube 28 is attached within a portion of distal head 26 at one or more adhesive points 30. An outer wall of guidewire tube 28 also may be attached to an inner wall of catheter body 22 at one or more guidewire tube/catheter body adhesive points 32. For example, in some embodiments tube/catheter body adhesive point 32 is located approximately 25 cm from the distal end of catheter body 22. Other embodiments may include one tube/catheter body adhesive point at approximately 25 cm from the distal end of catheter body 22 and another tube/catheter body adhesive point within approximately 1 cm of the distal end of catheter body 22. Any suitable adhesive point or combination of multiple adhesive points is contemplated.

Such attachment of guidewire tube 28 to both distal head 26 and catheter body 22 helps to hold distal head 26 in its position at the distal end of catheter body 22. Attachment also helps limit unwanted transverse motion of distal head 26 while allowing longitudinal motion due to tube elasticity. Adhesives used to attach guide wire tube 28 to distal head 26 and catheter body 22 may include, but are not limited to cyanoacrylate (eg. Loctite™, Loctite Corp., Ontario, CANADA or Dron Alpha™, Borden, Inc., Columbus, Ohio) or polyurethane (e.g. Dymax™, Dymax Engineering Adhesive, Torrington, Conn.) adhesives.

In still other embodiments, a portion of distal head 26 may be formed to extend laterally wider than the outer surface of catheter body 22 and guidewire tube 28 may be positioned on the outer surface of catheter body 22. Such embodiments, wherein guidewire tube 28 is positioned along the outer surface of catheter body 22, are commonly referred to as "monorail" catheters, as opposed to "over-the-wire" catheters as described by FIGS. 2 and 3. In addition to over-the-wire embodiments and monorail embodiments, ultrasound catheter 10 may also be configured as a combination or hybrid of over-the-wire and monorail embodiments. Specifically, such embodiments may include an ultrasound catheter 10 having a guidewire tube 28 formed through a distal portion of catheter body 22 only, with a guidewire entry/re-entry aperture being formed through a sidewall of catheter body 22 to permit passage of a guidewire from the distal guidewire lumen of the catheter to a position outside the catheter body.

With reference now to FIG. 2a, some embodiments of ultrasound catheter 10 include one or more fluid outflow apertures 36 in distal head 26 to permit fluid flow out of catheter body lumen 21. Other embodiments (not shown) may include one or more similar apertures at or near the distal end of catheter body 22, either in addition to or in place of apertures 36 in distal head 26. Outflow apertures 36 facilitate continual or intermittent passage of irrigant liquid through lumen 21, for example by infusion into lumen 21 via one or more side-arms 11, 13. Infusion of irrigant liquid through lumen 21, in proximity to ultrasound transmission member 24, may be used to control the temperature of ultrasound transmission member 24 to prevent overheating during use and enhance the process of disruption of blood vessel obstruction. Irrigant liquids may include, but are not limited to, saline and the like.

In some embodiments, guidewire tube 28 and lumen 29 are generally configured with an inner diameter slightly larger than the outer diameter of a guide wire along which catheter 10 is passed. Such a guidewire tube 28 may then be used as an alternative or additional means to allow fluid outflow through distal head 26. In still other embodiments, one or more separate lumens having separate outflow apertures formed at or near the distal tip of the catheter may be formed for infusion of oxygenated perfusate, medicaments or other fluids into the blood vessel or other anatomical structure in which the catheter is positioned.

Figure 4:
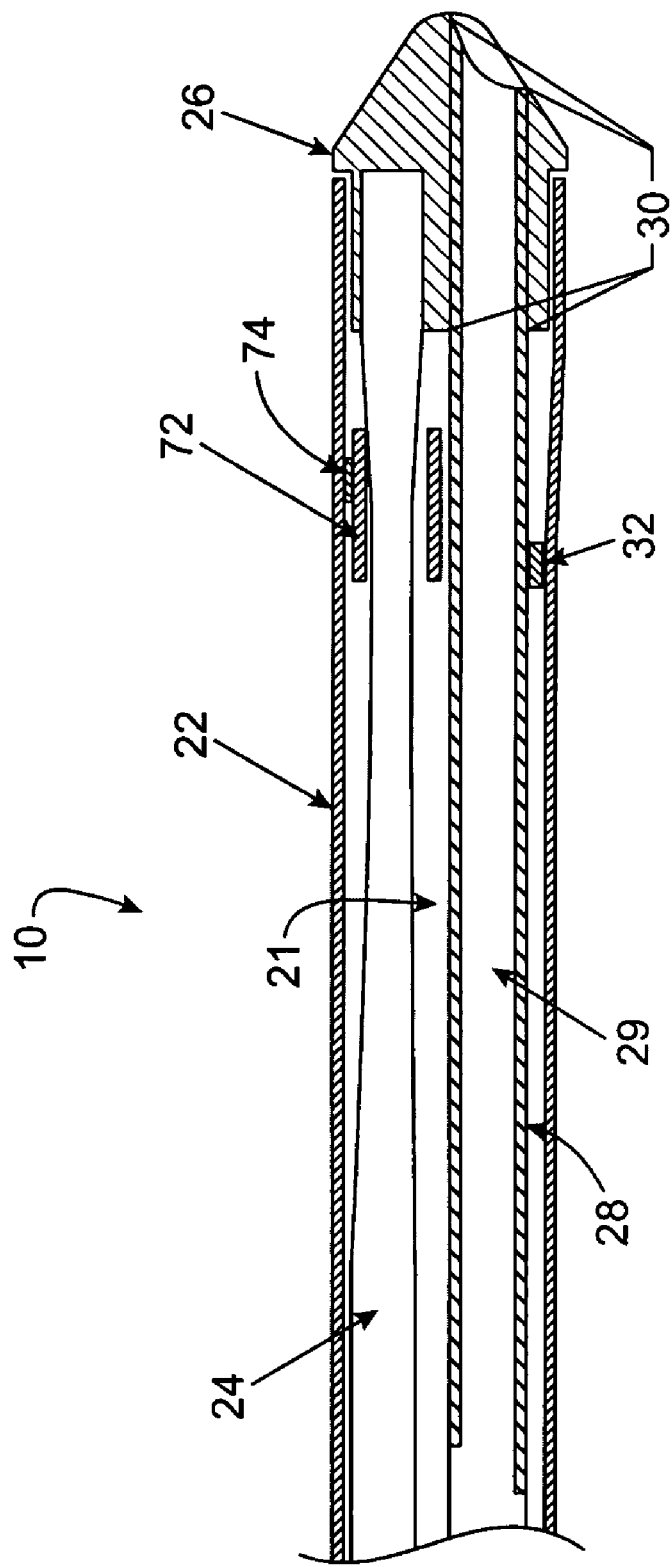
FIG. 4 is a cross-sectional view of a distal end of an ultrasound catheter device according to another embodiment of the present invention.

Referring now to FIG. 4, some embodiments of ultrasound catheter 10 include a distal sleeve 72 which is coupled with catheter body 22 and which surrounds a portion of ultrasound transmission member 24. Generally, distal sleeve 72 comprises a hollow cylindrical member, made of any suitable material, such as but not limited to a polymer. Sleeve 72 is coupled with catheter body 22 within lumen 21 at a location near the distal end of catheter body 22. Sleeve 72 may be coupled with body 22 via any reasonable means but will often by coupled via an adhesive at one or more adhesive points 74, such as those described above for coupling other components of catheter 10.

By surrounding a portion of ultrasound transmission member 24 and being coupled with catheter body 22, distal sleeve 72 adds stability to catheter 10. Although it is not necessary for use of catheter 10 and does not enhance the performance of catheter 10, physicians often twist or torque catheters radially upon insertion and/or during use of a catheter. Such twisting motions may cause guidewire tube 28 to kink and/or collapse as tube 28 moves in relation to catheter body 22 and transmission member 24. Placement of distal sleeve 72 around transmission member 24 causes the components of catheter 10 to move together when catheter 10 is twisted, thus avoiding kinking or collapsing of guidewire tube 28 and maintaining patency of guide wire lumen 29.

Figure 5:
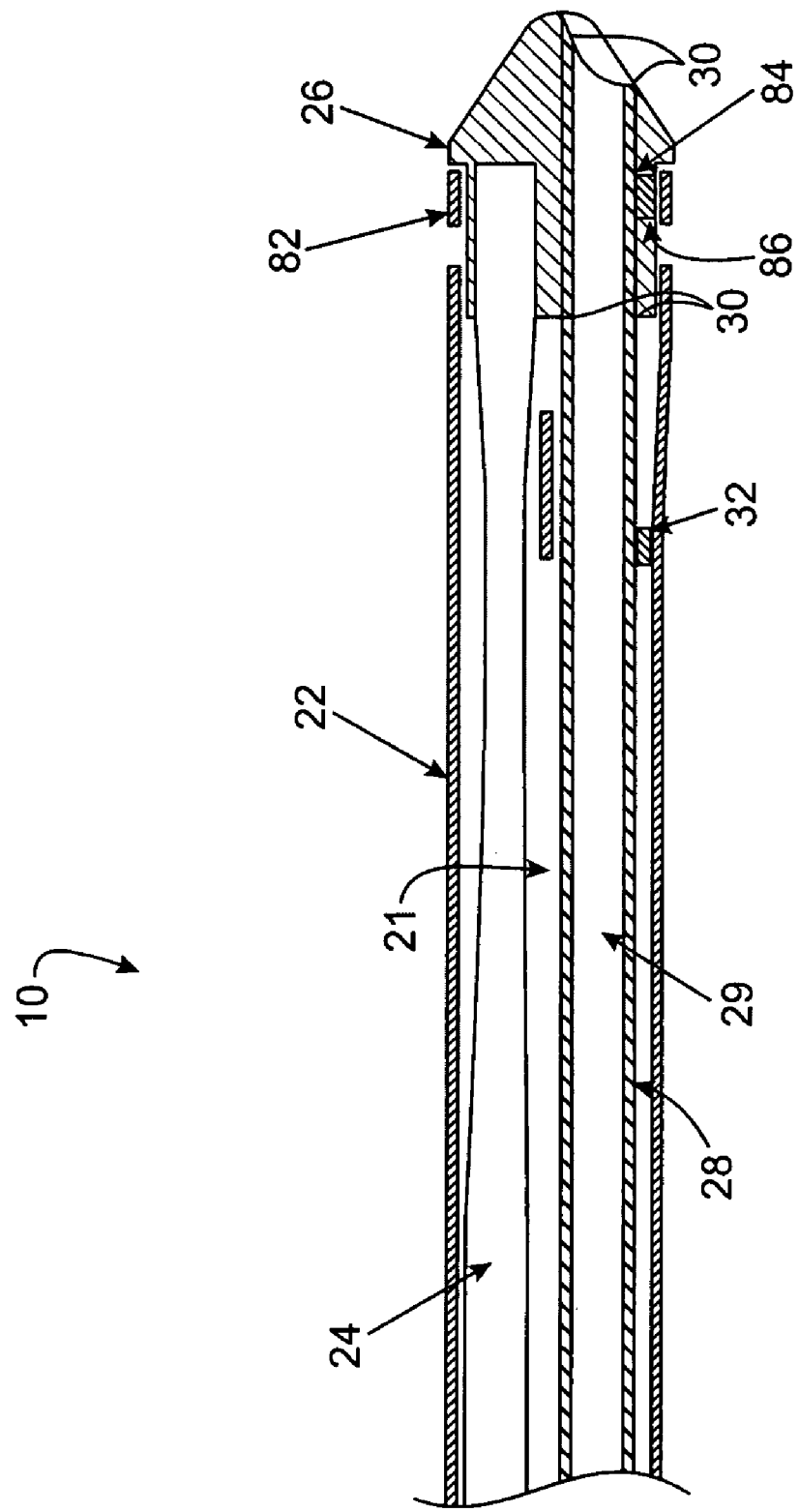
FIG. 5 is a cross-sectional view of a distal end of an ultrasound catheter device according to another embodiment of the present invention.

Referring now to FIG. 5, another embodiment of ultrasound catheter 10 includes a distal head sheath 82. Distal head sheath 82 is generally a cylindrical sheath that surrounds a portion of distal head 26. Sheath 82 is coupled with guidewire tube 28 via an adhesive at an adhesive point 84, which is accessed through a small hole 86 in a side portion of distal head 26. Sheath 82 may be made of any suitable material, but will typically be made of a polymer of the same or similar material with which guidewire tube 28 is made. Securing sheath 82 to tube 28 through hole 86 in distal head 26, enhances the stability of the connection between tube 28 and distal head 26. Thus, there is less chance that distal head 26 will break off from catheter 10 and safety of the device is enhanced. Forming sheath 82 and guidewire tube 28 from the same or similar materials will allow for a secure connection between the two via an adhesive.

Figure 5A:
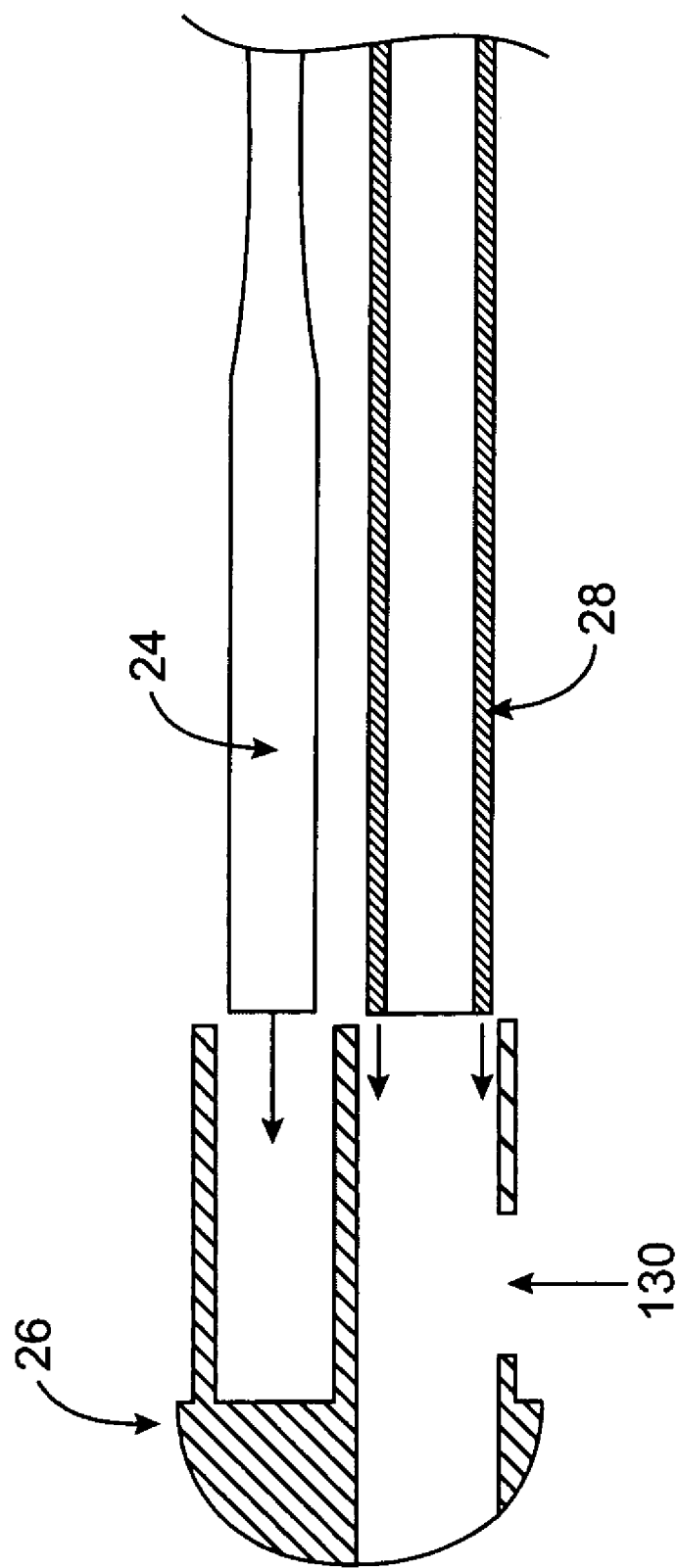
FIG. 5a is an exploded, cross-sectional, side view of a distal head, ultrasound transmission member and guidewire tube of an ultrasound catheter device according to an embodiment of the invention.

With reference to FIG. 5a, an exploded side view of distal head 26, ultrasound transmission member 24 and guidewire tube 28 is shown. In some embodiments, distal head 26 may include an opening 130, for facilitating the introduction of an adhesive. Opening 130 is typically larger than hole 86, described above, but may have any suitable configuration. In some embodiments, for example, opening 130 comprises a slot or similarly configured opening disposed around at least a portion of the circumference of distal head 26. Any other suitable configuration is contemplated within the scope of the invention, but opening 130 is generally configured to facilitate access through a portion of distal head 26 to allow introduction of one or more adhesive substances. Such adhesives, for example, may directly couple distal head 26 to guidewire tube 28, may couple sheath 82 (not shown in FIG. 5a) to guidewire tube 28 and/or the like. Enhanced adhesive coupling via opening 130 may enhance the useful life of catheter 10 by preventing detachment of distal head 28 from guidewire tube 28 or some other part of catheter 10.

Figure 6:
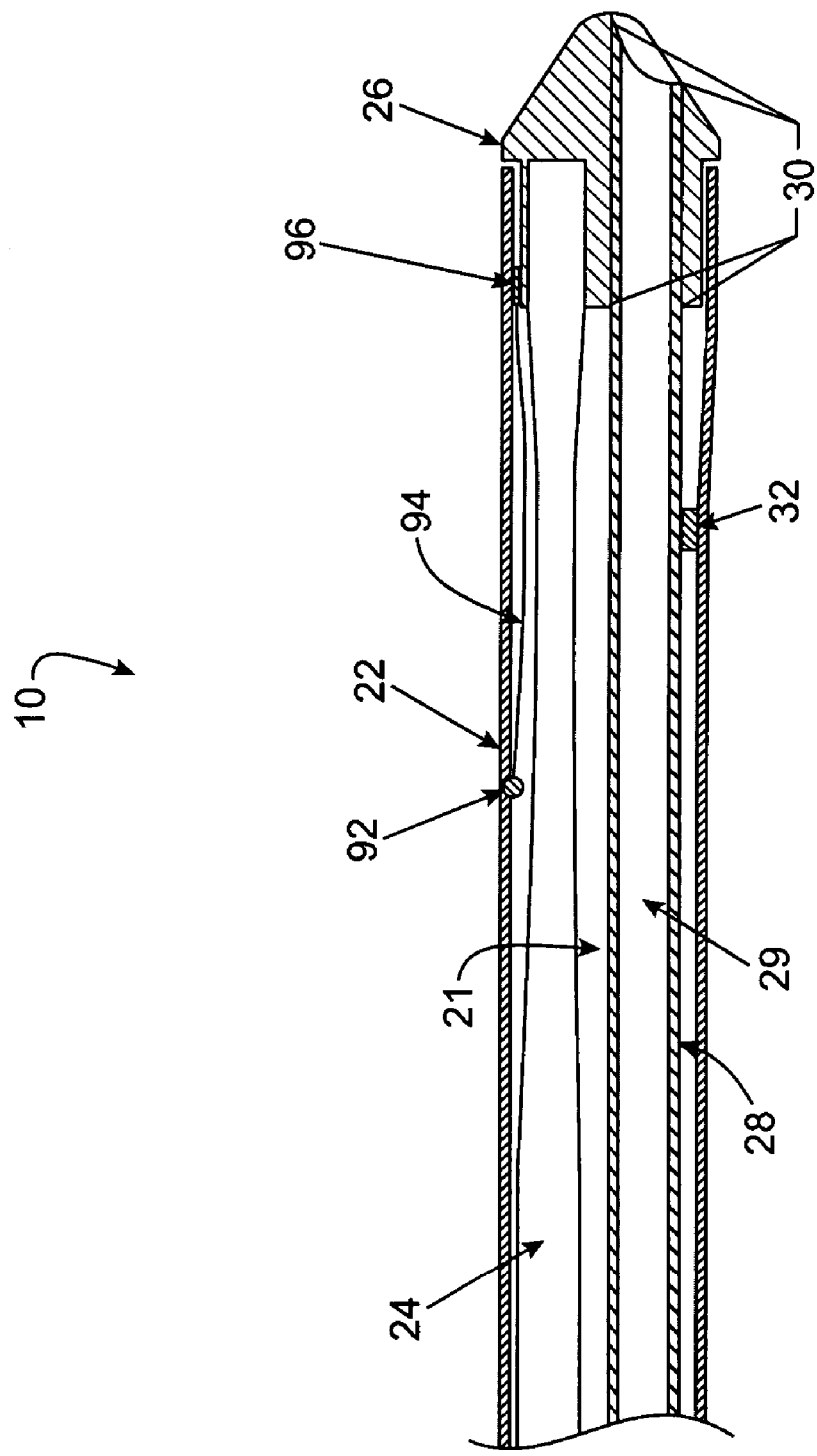
FIG. 6 is a cross-sectional view of a distal end of an ultrasound catheter device according to another embodiment of the present invention.

With reference now to FIG. 6, yet another embodiment of catheter 10 includes a distal head anchor 94. Distal head anchor 94 may comprise a wire or similar device made from metal, polymer or any other suitable material. Generally, a distal portion of anchor 94 is coupled with distal head 26 at an adhesive point 96, and a proximal portion of anchor 94 is coupled with catheter body 22 at an adhesive point 92 proximal to the extreme distal end of catheter body 22. Therefore, distal head 26 remains free-floating relative to the extreme distal end of catheter body 22 but is anchored to catheter body 22 at a more proximal location 92. This anchoring helps ensure that distal head 26 will not break off from catheter 10 during use. Any suitable anchoring device may be used and is contemplated within the scope of the invention.

Various types and designs of proximal end connector apparatus 12, ultrasound transducers 14, ultrasound generation devices 16 and/or the like may be coupled with ultrasound catheter 10 for use of catheter 10 to disrupt vascular occlusions. Detailed descriptions of such apparatus may be found, for example, in U.S. Pat. Nos. 5,267,954 and 5,380,274, invented by the inventor of the present invention and previously incorporated herein by reference. Therefore, the ultrasound catheters apparatus 20 and methods are not limited to use with any particular transducers 14, ultrasound generators 16, connector apparatus 12 or the like.

Figure 7:
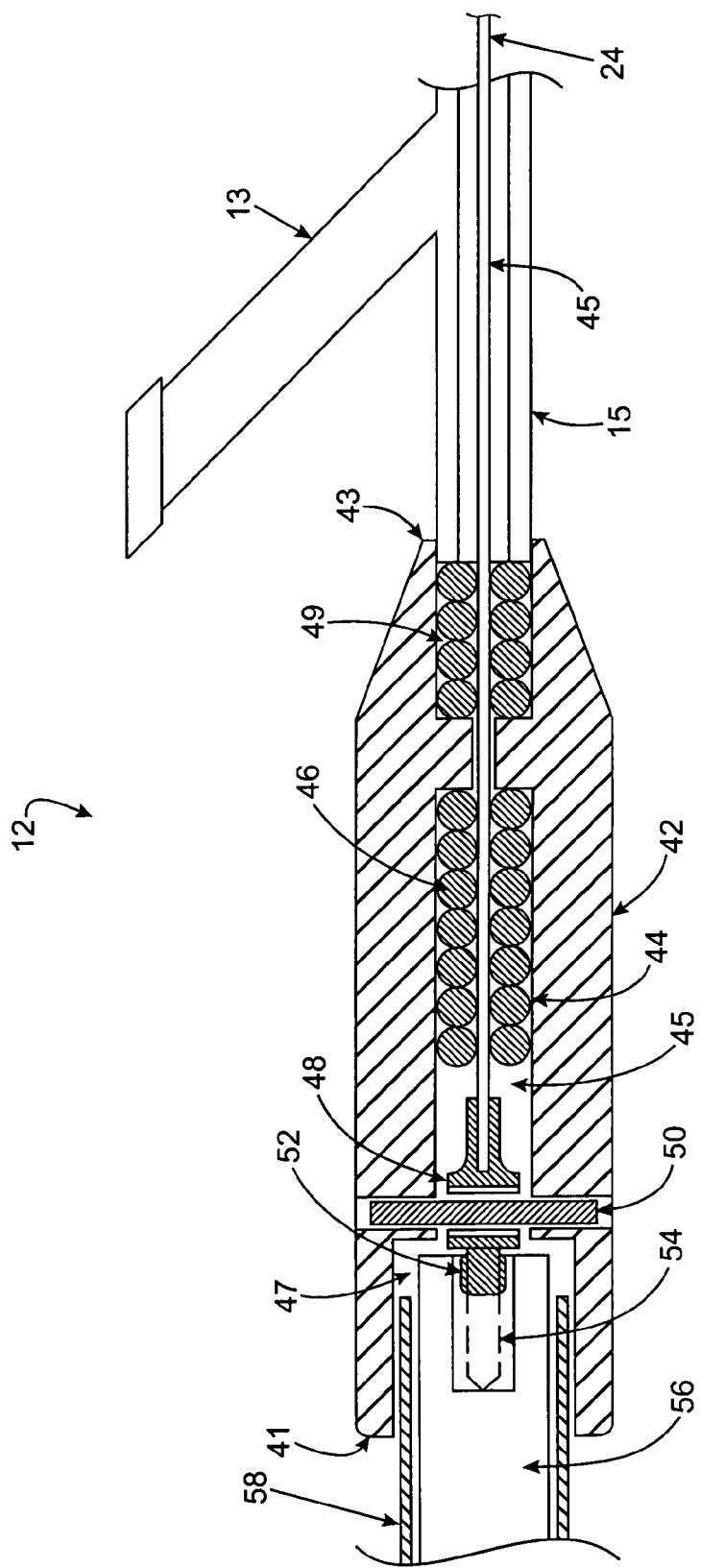
FIG. 7 is a cross-sectional view of a proximal connection assembly of an ultrasound catheter device according to an embodiment of the present invention.

That being said, and with reference now to FIG. 7, one embodiment of proximal end connector apparatus 12 suitably includes a housing 42 with a hollow inner bore 44. Bore 44 may have a uniform inner diameter along its length or, alternatively, may have multiple segments, such as a proximal segment 47, a middle segment 45 and a distal segment 49, each of which may surround one or more various components of proximal end connector apparatus 12.

Generally, proximal segment 47 of bore 44 is configured to allow attachment to ultrasound transducer 56, via transducer housing 58 and transducer thread 54. As such, proximal segment 47 includes a proximal portion of sonic connector 48, including a sonic connector thread 52 for connection with complementary transducer thread 54. Proximal segment 47 and/or the proximal end 41 of housing 42 may have any shape, diameter or configuration to allow coupling with transducer housing 58. As shown in FIG. 7, proximal segment 47 may have an inner diameter of a size to allow transducer housing 58 to fit within it. Thus, transducer housing 58 and proximal end 41 may be coupled via a pressure fit. In other embodiments, transducer housing 58 and proximal end 41 may connect via complementary threads. In still other embodiments, transducer housing 58 may fit around the outer diameter of proximal end 41. It should be apparent that any suitable configuration of proximal end may be used.

Similarly, sonic connector thread 52 may have any suitable size, shape and configuration for coupling with a complementary transducer thread 54. Such coupling may be achieved via complementary threads, snap-fit mechanism, or any other suitable means. Otherwise, sonic connector thread 52 and sonic connector 48 are generally configured to transmit ultrasound energy from ultrasound transducer 56 to ultrasound transmission member 24. A pin 50 is generally positioned within sonic connector 48 and is disposed between proximal segment 47 and middle segment 45 of bore 44.

Middle segment 45 of bore 44 typically surrounds a portion of sonic connector 48, which is coupled with the distal end of ultrasound transmission member 24, and one or more sets of absorber members 46, which surround a portion of ultrasound transmission member 24 to reduce vibration of member 24. Absorber members 46 may include, for example, one or more O-rings. Sonic connector 48 is coupled with the distal end of ultrasound transmission member 24 by any suitable means, to transmit ultrasound energy to member 24 from transducer 56.

Absorber members 46 are configured to circumferentially surround ultrasound transmission member 24 in whole or in part to dampen transverse vibrations created by the transmission of ultrasound energy. The number, size and configuration of absorber members 46 used may be determined based upon a desired level of dampening and any suitable configuration or combination may be used. Alternatively, other dampening structures may be used, rather than absorber members 46, and thus the configuration of proximal connector apparatus 12 is not limited to the use of one or more sets of absorber members 46.

Distal segment 49 of bore 44 typically surrounds a portion of ultrasound transmission member 24 and may also contain one or more additional sets of absorber members 46. Distal segment 49 may also contain a portion of connector device 15, which is coupled with the distal end 43 of housing 42 of proximal end connector apparatus 12. Again, connector device 15 may comprise a Y-connector as in FIGS. 7 and 7a, a W-connector as in FIGS. 8 and 8a, or any other suitable connector device. Coupling of connector device 15 with distal end 43 of apparatus 12 may be accomplished via complementary threads, pressure fitting, or any other suitable means. A common lumen 45 of connector device 15 allows passage of ultrasound transmission member 24 and is in communication with catheter body lumen 21.

Connector device 15 may include an infusion arm 13 to allow for introduction and/or withdrawal of one or more fluids for irrigation, dye injection and/or the like. Connector device 15 may further include additional arms, as described more fully below, for passage of a guide wire and/or passage of any other suitable structure or substance through catheter 10. In some embodiments, infusion arm 13 is in fluid communication with common lumen 45 and catheter body lumen 21. In other embodiments, arm 13 may have a lumen that communicates with a separate lumen in connector device 15 and catheter body 22.

Generally, pressurized fluid such as an irrigant liquid may be infused through infusion arm 13, common lumen 45 and catheter body lumen 21 so that it flows out of fluid outflow apertures 36. The temperature and flow rate of such irrigant liquid may be specifically controlled to maintain the temperature of ultrasound transmission member 24 at a desired temperature within its optimal working range and/or may enhance disruption of blood vessel occlusions. In particular, in embodiments of the invention wherein ultrasound transmission member 24 is formed of a metal alloy which exhibits optimal physical properties (e.g. super elasticity) within a specific range of temperatures, the temperature and flow rate of irrigant liquid infused through infusion arm 13 may be specifically controlled to maintain the temperature of ultrasound transmission member 24 within a range of temperatures at which it demonstrates its most desirable physical properties. For example, in embodiments of the invention where ultrasound transmission member 24 is formed of a shape memory alloy which exhibits super elasticity when in its martensite state, but which loses super elasticity as it transitions to an austenite state, it will be desirable to adjust the temperature and flow rate of the irrigant liquid infused through infusion arm 13 so as to maintain the shape memory alloy of ultrasound transmission member 24 within a temperature range at which the alloy will remain in its martensite state and will not transition to an austenite state. The temperature at which such shape memory alloys transition from a martensite state to an austenite state is known as the "martensite transition temperature" of the material. Thus, in these embodiments, the fluid infused through arm 13 will be at such temperature, and will be infused at such rate, as to maintain the shape memory alloy of ultrasound transmission member 24 below its martensite transition temperature.

Figure 7A:
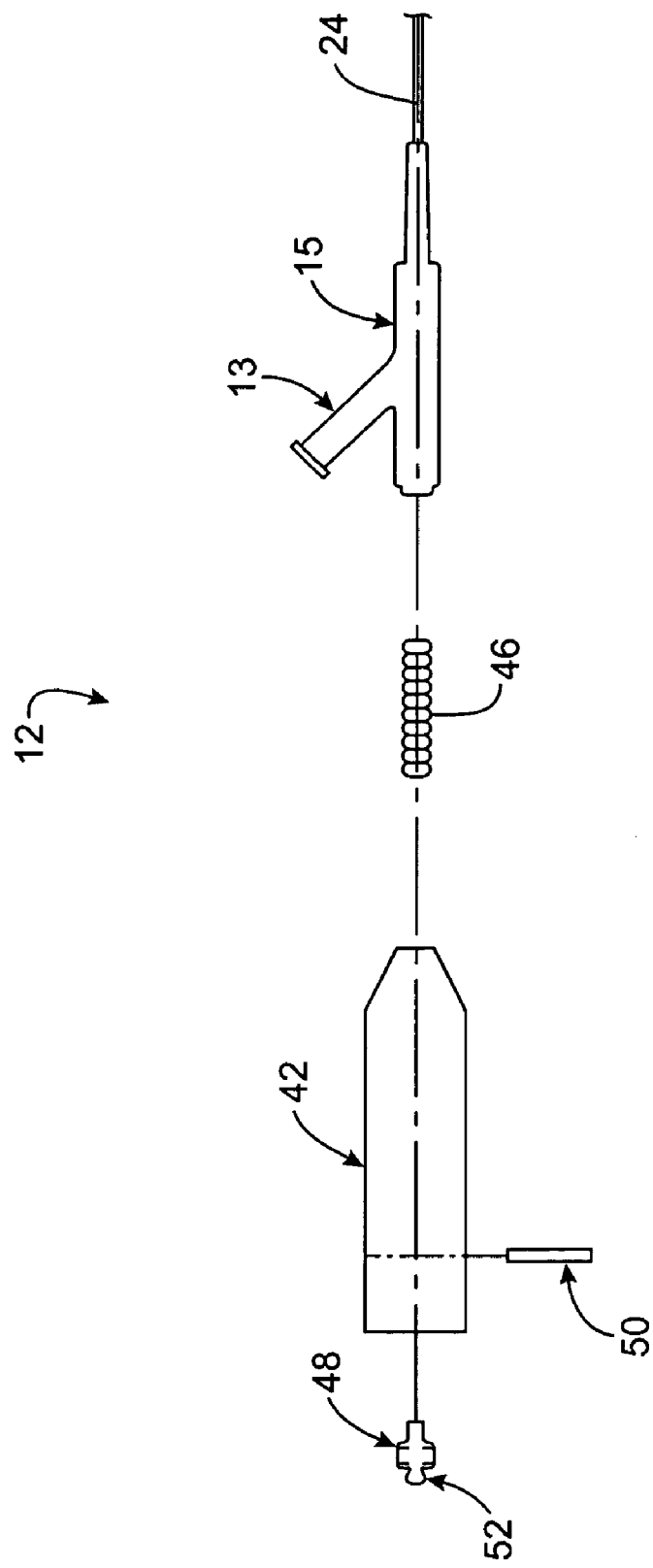
FIG. 7a is an exploded side view of a proximal connection assembly as in FIG. 7.

Referring now to FIG. 7a, proximal end connector apparatus 12 is shown in exploded side view. In this embodiment, sonic connector 48 is held within housing 42, by means of dowel pin 50. In other embodiments, dowel pin 50 may not be included and sonic connector 48 may be positioned within housing by other means. Otherwise, FIG. 4a simply demonstrates the various components previously described with reference to FIG. 4.

Figure 8:
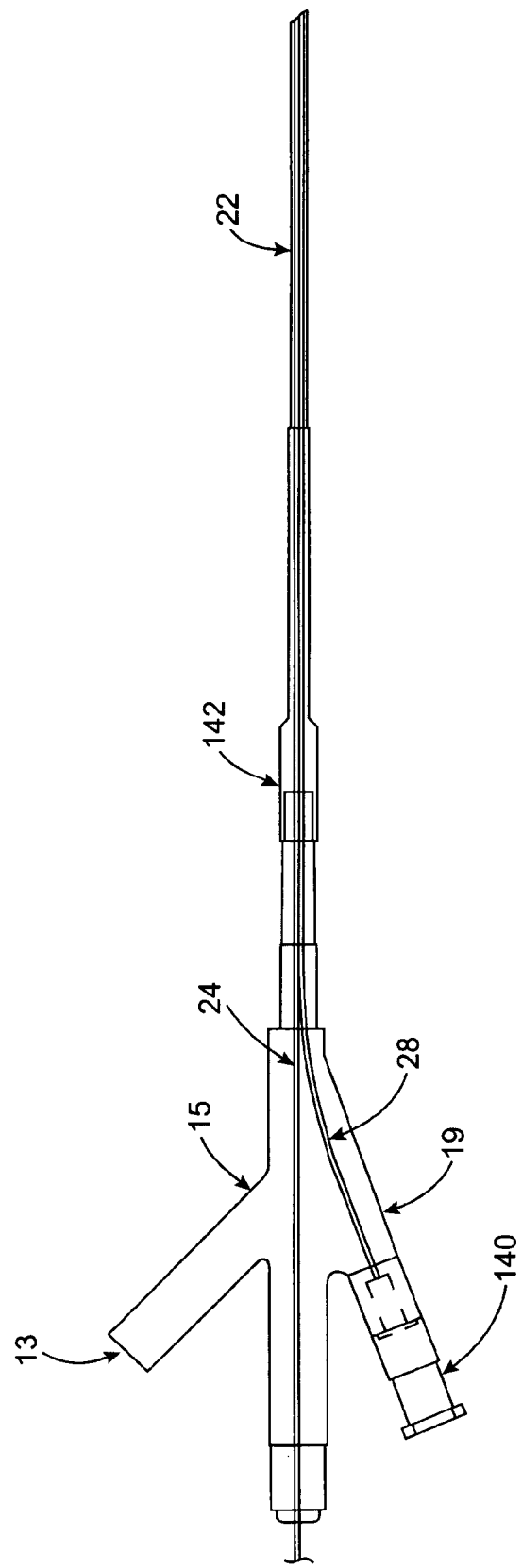
FIG. 8 is a side view of a proximal end of an ultrasound catheter device coupled with a connector device according to an embodiment of the present invention.

With reference now to FIG. 8, in some embodiments a proximal end of catheter 10 may be coupled with connector device 15 that comprises a W-connector. Connector device 15 may include infusion arm 13, guidewire arm 19 and a guidewire port 140 coupled with guidewire arm 19. In some embodiments, a coupling device 142 is used for coupling connector device 15 with catheter body 22. Coupling device may comprise, for example, a sheath, sleeve or any other suitable device. Connector device 15 may also comprise any suitable connector, including any configuration of ports, lumen(s) and the like. In some embodiments, for example, guidewire arm 19 will have an angle that is as slight as possible, relative to the longitudinal axis of catheter body 22, so that only a minimal bending of a guidewire occurs when the guidewire is inserted into guidewire arm 19 and guidewire lumen 28.

Figure 8A:
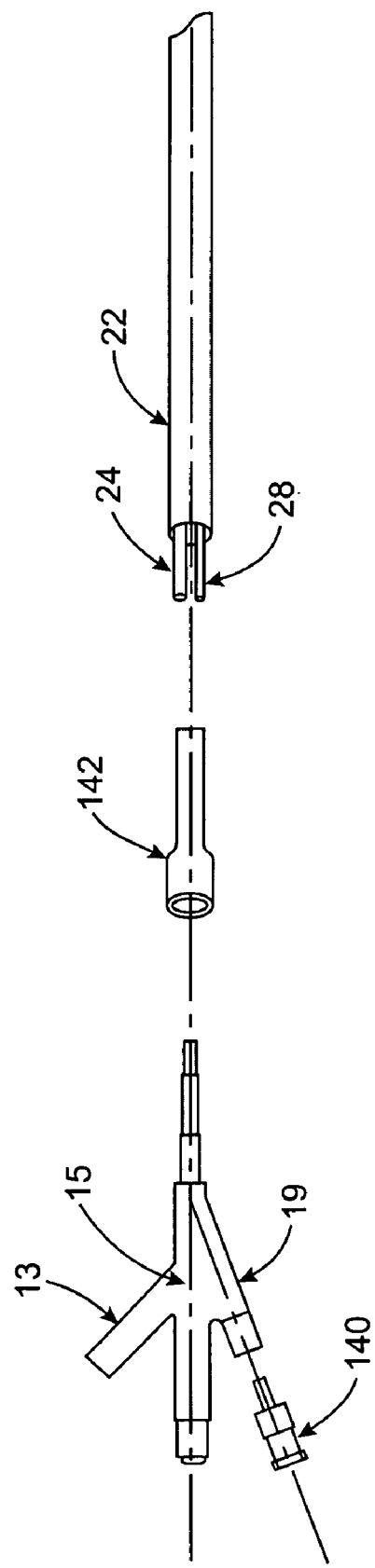
FIG. 8a is an exploded, side view of a proximal end of an ultrasound catheter device and a connector device according to an embodiment of the present invention.

FIG. 8a shows an exploded view of connector device 15 and a proximal portion of catheter body 22, as in FIG. 8. This view shows one embodiment of how coupling device 142 may be used to coupled catheter body 22 with connector device 15. In other embodiments, various alternative coupling means may be employed without departing from the scope of the present invention.

In some embodiments, ultrasound catheter 10, one or more components of catheter 10 and/or one or more additional components of ultrasound system 20 may be sterilized using an electron-beam sterilization technique. Electron-beam sterilization techniques are known. For example, one may refer to "Electron-Beam Systems for Medical Device Sterilization," by L. R. Calhoun et al., at www.devicelink.com/mpb/archive/97/07/002.html, the entire contents of which is hereby incorporated by reference. Electron-beam radiation has not been applied for sterilization of devices such as ultrasound catheter 10 of the present invention. Such sterilization techniques may provide significant advantages by exposing catheter 10 to less stress than would occur with traditional sterilization methods.

Although the invention has been described above with specific reference to various embodiments and examples, it should be understood that various additions, modifications, deletions and alterations may be made to such embodiments without departing from the spirit or scope of the invention. Accordingly, it is intended that all reasonably foreseeable additions, deletions, alterations and modifications be included within the scope of the invention as defined in the following claims.

What is claimed is:

1. A method of making an ultrasound catheter for disrupting occlusions in blood vessels, the method comprising:
    forming a catheter body over a mandrel, wherein the mandrel includes at least one bend for forming a corresponding bend in the catheter body;
    separating the catheter body from the mandrel;
    inserting an ultrasound transmission member into a lumen of the catheter body, wherein inserting the ultrasound transmission member reduces an angle of the at least one bend in the catheter body;
    coupling a distal head with the ultrasound transmission member, such that at least a portion of the distal head extends distally beyond a distal end of the catheter body; and
    coupling an ultrasound transducer with the ultrasound transmission member, such that ultrasonic energy provided from the ultrasound transducer is transmitted to the ultrasound transmission member and the distal head.

2. A method as in claim 1, wherein forming catheter body comprises forming the body over a mandrel having a bend of between about 20 degrees and about 90 degrees.

3. A method as in claim 1, wherein inserting the ultrasound transmission member into the lumen reduces the angle of the bend in the catheter body to between about 15 degrees and about 80 degrees.

4. A method as in claim 1, wherein inserting the ultrasound transmission member into the lumen causes the ultrasound transmission member to bend at the bend in the catheter body.

5. A method as in claim 4, wherein the ultrasound transmission member bends at an angle less than the angle of the bend in the catheter body.

6. A method as in claim 1, further comprising placing a sheath over at least a portion of the catheter body to maintain the bend in the catheter body.

7. A method as in claim 1, further comprising directing an electron beam at the ultrasound catheter to sterilize the catheter.

8. A method as in claim 1, wherein the ultrasound transducer is coupled with the ultrasound transmission member via a sonic connector, such that ultrasonic energy provided by the ultrasound transducer is transmitted to the ultrasound transmission member via the sonic connector.

9. A method of making an ultrasound catheter for disrupting occlusions in blood vessels, the method comprising:
    placing a catheter body over a mandrel, wherein the mandrel includes at least one bend for forming a corresponding bend in the catheter body;
    heating the catheter body;
    removing the catheter body from the mandrel;
    inserting an ultrasound transmission member into a lumen of the catheter body, wherein inserting the ultrasound transmission member reduces an angle of the at least one bend in the catheter body;
    coupling a distal head with the ultrasound transmission member, such that at least a portion of the distal head extends distally beyond a distal end of the catheter body; and
    coupling a sonic connector with the ultrasound transmission member, such that ultrasonic energy provided to the sonic connector is transmitted to the ultrasound transmission member and the distal head.

10. A method as in claim 9, wherein placing catheter body comprises placing the body over a mandrel having a bend of between about 20 degrees and about 90 degrees.

11. A method as in claim 9, wherein inserting the ultrasound transmission member into the lumen reduces the angle of the bend in the catheter body to between about 15 degrees and about 80 degrees.

12. A method as in claim 9, wherein inserting the ultrasound transmission member into the lumen causes the ultrasound transmission member to bend at the bend in the catheter body.

13. A method as in claim 12, wherein the ultrasound transmission member bends at an angle less than the angle of the bend in the catheter body.

14. A method as in claim 9, wherein the ultrasound transmission member remains straight after inserting the ultrasound transmission member into the lumen.

15. A method as in claim 9, further comprising placing a sheath over at least a portion of the catheter body to maintain the bend in the catheter body.

16. A method as in claim 9, further comprising directing an electron beam at the ultrasound catheter to sterilize the catheter.

* * * * *

UNITED STATES PATENT AND TRADEMARK OFFICE
CERTIFICATE OF CORRECTION

PATENT NO. : 7,604,608 B2  Page 1 of 1
APPLICATION NO. : 10/345078
DATED : October 20, 2009
INVENTOR(S) : Nita et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1237 days.

Signed and Sealed this

Fifth Day of October, 2010

David J. Kappos
*Director of the United States Patent and Trademark Office*